United States Patent
Markus

(10) Patent No.: US 8,647,335 B2
(45) Date of Patent: Feb. 11, 2014

(54) LASER APPLICATOR

(75) Inventor: Kai Ulf Markus, Alsdorf (DE)

(73) Assignee: Vimecon GmbH (DE)

( * ) Notice: Subject to any disclaimer, the term of this patent is extended or adjusted under 35 U.S.C. 154(b) by 1134 days.

(21) Appl. No.: 12/226,147

(22) PCT Filed: Mar. 16, 2007

(86) PCT No.: PCT/EP2007/052524
§ 371 (c)(1),
(2), (4) Date: Oct. 9, 2008

(87) PCT Pub. No.: WO2007/118745
PCT Pub. Date: Oct. 25, 2007

(65) Prior Publication Data
US 2009/0275931 A1    Nov. 5, 2009

(30) Foreign Application Priority Data
Apr. 11, 2006    (DE) .......................... 10 2006 016 957

(51) Int. Cl.
*A61B 18/18*    (2006.01)

(52) U.S. Cl.
USPC .............................................. 606/15; 606/16

(58) Field of Classification Search
USPC ...................................... 604/258; 606/15, 16
See application file for complete search history.

(56) References Cited

U.S. PATENT DOCUMENTS

| | | | | |
|---|---|---|---|---|
| 4,784,132 A | * | 11/1988 | Fox et al. | 606/15 |
| 5,632,767 A | * | 5/1997 | Sinofsky | 607/89 |
| 5,957,882 A | * | 9/1999 | Nita et al. | 604/22 |
| 6,454,758 B1 | * | 9/2002 | Thompson et al. | 604/528 |
| 6,676,656 B2 | * | 1/2004 | Sinofsky | 606/16 |
| 7,386,203 B2 | * | 6/2008 | Maitland et al. | 385/27 |
| 2006/0018596 A1 | * | 1/2006 | Loebel | 385/38 |

FOREIGN PATENT DOCUMENTS

| | | |
|---|---|---|
| DE | 44 25 195 C1 | 11/1995 |
| EP | 0 689 797 A1 | 1/1996 |
| WO | WO 96/07451 A2 | 3/1996 |
| WO | WO 2006/019510 A1 | 2/2006 |

* cited by examiner

*Primary Examiner* — Bill Thomson
*Assistant Examiner* — Nathan J Jenness
(74) *Attorney, Agent, or Firm* — Miles & Stockbridge PC

(57) ABSTRACT

A laser applicator has a catheter (12) that contains a optical fiber and a lateral decoupling area at the distal end. The end section of the strand is preformed to a loop (16) the plane of which runs crosswise to the main section (14) of the strand. This makes possible an extensive linear introduction of laser energy into the surrounding tissue. The invention is suited especially for the treatment of arrhythmia.

8 Claims, 4 Drawing Sheets

LASER APPLICATOR

BACKGROUND OF THE INVENTION

The invention refers to a laser applicator comprising an optical fiber that extends in a strand-shaped sheath and comprises a lateral decoupling area in a distal end portion, the sheath being formed as a loop in the area of the end portion, wherein the plane of the loop extends transverse to the major part of the sheath.

Atrial fibrillation is the most frequent cardiac arrhythmia in Europe and North America, afflicting more than every 15$^{th}$ human older than 60 years of age. Electric excitation waves are generated in the cardiac vestibules (atria) that propagate chaotically and impair the pumping function of the heart. Typical medical conditions are subjectively felt cardiac arrhythmias, tachycardia and a limitation of the physical load capacity, dizziness and fainting spells. Without a therapy, strokes will occur, often with serious and even fatal consequences, since blood clots can form due to an insufficient movement of the cardiac wall during atrial fibrillation, which may cause embolisms.

Methods using catheters to treat atrial fibrillation offer a chance for a permanent success of the therapy without requiring further permanent medication. Here, the source of the arrhythmia is searched for in heart using a thin flexible catheter and is then sclerosed.

In methods using catheters, certain electrically active regions of the atrial tissue are approached and obliterated by applying current. Eliminating or isolating these regions can prevent the occurrence of atrial fibrillation in 60%-80% of the cases. To achieve this, multiple punctual applications of current are used to form circular scars in the left atrium, which electrically insulate the affected cardiac tissue from the rest. This method is called "pulmonary vein isolation". A conventional catheter is first advanced into the right atrium. In order to reach the left side, the interatrial septum is pierced (transeptal puncture). By limiting the conventional catheters to punctual lesions, an isolation line is formed by points that must be assembled to form circles in a three-dimensional space under two-dimensional X-ray control, without leaving gaps or injuring healthy tissue. More recent techniques aim at obtaining circular lesions around the pulmonary veins using balloon systems that are expanded at the pulmonary veins and extend into the same. The energy (ultrasound, laser energy, cold) is emitted within the balloon and is passed to the outer side thereof. The system of the present invention operates without a balloon whereby it may be much more compact.

A laser applicator is described in U.S. Pat. No. 6,676,656 B2. Among other applications, this laser applicator serves for the treatment of arrhythmias. It comprises a hand-held housing with a sheath extending from the distal end thereof, which sheath contains a light guide. The sheath may be wound around a plurality of pulmonary veins, wherein radiation from the decoupling portion of the light guide impinges on the wrapped pulmonary veins and scleroses the same. The laser applicator is suitable only for use at the open heart, in particular in connection with the placing of bypasses. This is a major limitation of the applicability of the device. Further, larger distances occur between the light guide and the target region to be treated, so that a comparatively high irradiation power is required.

DE 198 03 460 C1 describes an application device for the treatment of biological tissue through laser radiation. In a distal end portion, a light guide enclosed by a sheath layer is at least partly free of this sheath layer such that the laser radiation is emitted sideward from the fiber core with a homogenous propagation. At the exit points. The light guide has light-scattering particles. The distribution of the intensity of the energy exiting from the strand can be influenced by changing the particle density.

DE 101 29 029 A1 describes the introduction of laser light into a optical fiber including scattering bodies to obtain a diffuse lateral irradiation.

DE 44 07 498 C2 describes an optical waveguide for lighting purposes that decouples light sideward. For this purpose, the surface of the optical sheath is textured.

Finally, EP 1 527 798 A2 describes a laser applicator for photo therapy, which also includes scattering particles in a distal end portion of the optical fiber.

SUMMARY OF THE INVENTION

It is an object of the present invention to provide a laser applicator with which a blood vessel or a tubular organ can be sclerosed in an annular form, so as to preclude the transmission of electrical signals by isolation.

The laser applicator of the present invention includes a sheath of the optical fiber which is part of an elongate flexible catheter that is stretchable so as to be advanced to the destination through a tube or over a guide wire. The shape of the laser applicator is similar to a flying lariat. It forms a loop at its end that may be placed in a blood vessel and/or hollow organ such that it is in contact with the circumferential wall.

By laterally decoupling the laser energy out from the optical fiber, the laser energy is induced into the adjacent tissue in a well-aimed manner. Like a conventional catheter, the laser applicator may be introduced intravascularly into the heart, i.e. through the vascular system of a patient, so that the heart need not be opened. Thus, the operation can be minimally invasive.

The laser applicator of the present invention is particularly suitable for the treatment of atrial fibrillation. It is adapted to sclerose cardiac tissue by transforming light energy into thermal energy. The laser radiation exiting from the optical fiber heats the surrounding tissue to values above 60° C., leading to denaturalization of proteins and to the formation of an electrically inactive scar. In the process, laser light penetrates into the tissue and is transformed into heat by absorption at the chromophores (e.g. blood and muscle pigments, haemoglobin, myoglobin). Depending on the chromophore concentration and the wavelength of the light, the light penetrates the tissue for a few millimeters, however, while being scattered to a great extent. Especially for the treatment of cardiac tissue, such as an ablation for the treatment of cardiac arrhythmias, it is required that the maximum extension of the thermal lesion, and thus of the scar, is not immediately at the application site of the energy, i.e. the inner side of the heart. In this context, interactions with the flowing blood and a possible cooling by leaking liquid, typically a physical sodium solution, are of great importance.

Moreover, it is of importance with many cardiac arrhythmias to electrically isolate contiguous areas by forming scars of linear, circular or other shapes. At present, this is achieved mostly by successively arranged punctual lesions (most often by emitting current).

The system of the invention serves to guide ("decouple") laser light from a catheter such that areas of linear, circular or other shapes can be treated with this energy without having to move the catheter system or individual components of the system during the application or without having to change the position thereof.

The loop describes a circumferential range of more than 180°. Preferably, it extends over 360° so that a closed annular scar is obtained in a vessel or a hollow organ. A closed annular shape is not necessary in all instances, however.

The laser light applicator is flexible, however, it has a deformation or a shape memory. For an introduction into the body, it is straightened by force and advanced to the destination through a lock or via a guide wire, for example. Thereafter, the guiding device is removed, whereby the catheter restores to a predetermined initial shape.

In a preferred embodiment of the invention it is preferred that, seen in cross section of the strand, the decoupling region is mainly or exclusively directed outward from the loop. Thereby, the highest energy density is achieved just beneath the tissue surface when the catheter abuts on the tissue. This is important for a minimization of the denaturalization and carbonization of the blood components and the tissue surface, which depend on the density of the energy.

Besides forming a circle for the formation of circular coagulation necroses, the loop may also be configured such that lines, arcs or other structural shapes are produced. This may be suitable in electrically isolating pulmonary veins, for example, in the case of atrial arrhythmia, as well as in performing substrate modifications in the left atrium.

A lateral decoupling of the laser radiation from the optical fiber may be effected in different ways. Prior art offers numerous possibilities in this respect. One of these possibilities provides that the refraction index of the light guide core is made greater than that of the surrounding sheath in the remaining portion so that in the decoupling region no total reflection occurs anymore and the light exits sideward. Another possibility is to increase the refraction index of the surrounding sheath at the exit point with respect to that of the fiber core in the transmitting part of the light guidance phase.

The directed decoupling of the energy from the strand can also be effected in various manners, for example, by providing a longitudinally extending strip of the circumference of the fiber sheath with a refraction index differing from the rest of the sheath's circumference. This may be achieved by extrusion of different materials. As an alternative, a part of the circumference of the sheath material can be removed or molten with the underlying layer of the fiber core which leads to a change in the refraction index at this site. Another sheath material, e.g. with a higher refraction index, may be applied onto the core fiber now partly clad.

Another possibility causing a decoupling of light by changing the refraction index of the fiber core and the sheath, is the application of a further material with a higher refraction index on the non-clad fiber core material. The rest of the segment of a circle is covered with a material having a low refraction index that reflects light from the boundary surface. In particular, this arrangement may be realized by introducing a core fiber into a catheter tube and fastening it at the tube wall having the higher refraction index. The remaining lumen is filled with another material having a lower refraction index, e.g. water, which may also be used for rinsing purposes.

Finally, it is possible to limit the exit angle of the light from the fiber by applying materials on the surface.

To achieve a uniform energy distribution over the length of the decoupling distance, the angle of the circle segment of the sheath that causes the decoupling may be changed over the length of the decoupling distance. Further, the angle of the circle segment may be determined by a reflective layer applied on the core fiber or the fiber sheath.

An alternative possibility of influencing the exiting radiation intensity is to change the coefficient of the refraction index between the core and the sheath over the length of the decoupling region. This can further be achieved by introducing additional materials, e.g. silicon dioxide nano-particles, into a plastic material so that the refraction index changes in the axial direction. Finally, it is also possible to introduce silicone or another mass in a viscous phase into the catheter tube.

Another possibility of influencing the exiting radiation energy is the introduction of stepped decouplers over the strand length of the laser light applicator. Stepped decouplers cause a stepped partial decoupling of the laser energy from a light guidance phase by making notches in the core fiber surface. The fiber end is provided with a reflector reflecting the residual portion of the laser light into the fiber.

Finally, the exiting radiation energy can be controlled by means of reflection or absorption in the fiber material.

The laser applicator should be as flexible as possible. On the other hand, the curvature radius of optical fibers is limited. To solve this problem, the optical fiber may include a plurality of parallel optical fibers. Since the energy has to be "distributed" over a plurality of fibers in order not to exceed the maximum product of effective surfaces of the individual optical fibers, a plurality of fibers with a core diameter of 10-50 µm, for example, are used, which emit their energy into the laser applicator and then into the surrounding tissue by lateral decoupling. These fibers may be side by side and may each emit energy over the entire length of the laser applicator. As an alternative, the fibers may be arranged such that a respective fiber supplies laser energy to a part of the length of the applicator and then ends. Another fiber, situated inward in the applicator, is led outward to the applicator and emits laser light over another part of the total length of the laser light applicator. Both possibilities may be used in combination to guarantee a uniform axial and radial decoupling of the laser light from the laser light applicator.

Since the in-coupling losses are high when a diode laser is used, this arrangement is especially suited for use with a fiber laser system.

When laser light decoupled from an optical fiber is used, the maximum energy density of the laser light decreases as the distance from the decoupling site increases and is usually the highest at the site of decoupling. However, this may have the effect that structures near the laser applicator have to absorb high thermal energies in order to achieve the desired effect in depth. In particular, coagulation and carbonization may occur at the surface of the tissue. Since carbonized surfaces absorb laser light completely and thereby reinforce the undesirable effect of an excessive heating at the surface, this effect should be avoided.

According to a preferred embodiment of the invention, the light radiation is focussed on a focal point in the depth of the tissue, remote from the applicator and the catheter surface. Due to scattering in the tissue, no exactly defined focussing is possible. Nevertheless, the preferential direction of the beam propagation in the tissue can be defined by focussing. This results in a maximum of effect and absorption that leads to a heating of the tissue typically at a few millimeters from the applicator.

The following is a detailed description of embodiments of the invention with reference to the drawings.

DETAILED DESCRIPTION OF THE PREFERRED EMBODIMENTS

Figure 1:
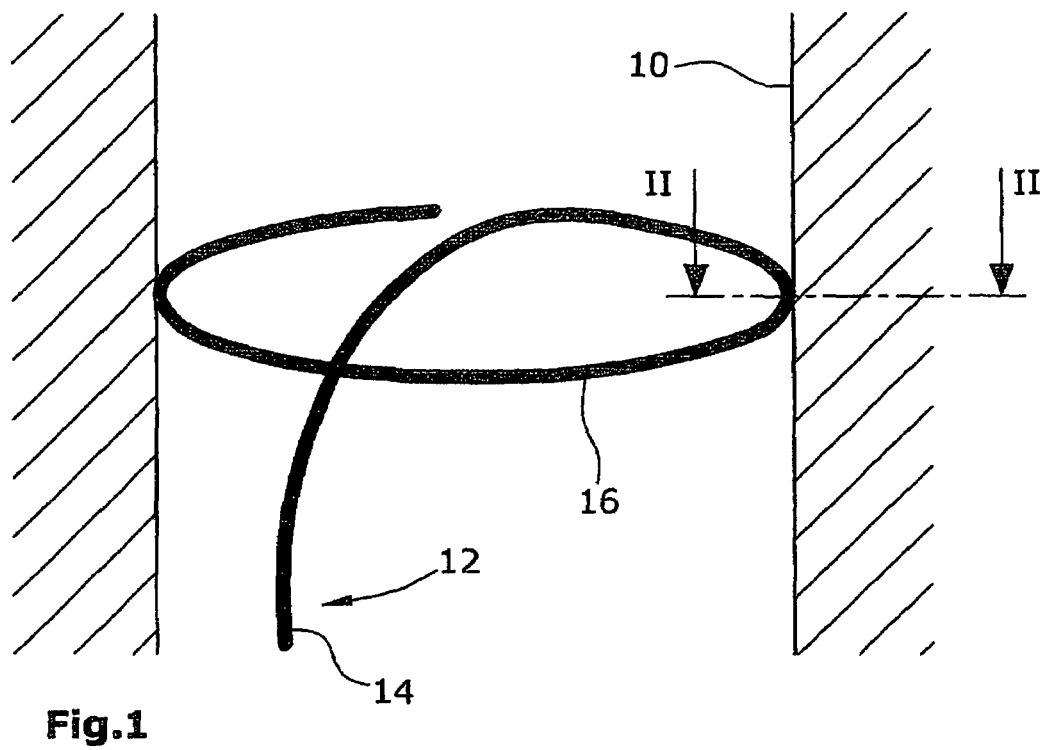
FIG. 1 is a schematic illustration of the laser applicator in a blood vessel.

FIG. 1 illustrates a tubular blood vessel 10 whose wall is to be treated thermally by means of the laser applicator. The laser applicator comprises a catheter 12 in the form of an elongate strand. The catheter may comprise one or a plurality of lumens, but it may also be free of cavities. The catheter 12 is pre-formed in the manner schematically illustrated in FIG. 1. It has a main part 14 which is substantially straight, and a loop 16 forming a circle open at one location. While the main part 14 extends longitudinally in the blood vessel, the loop 16 is positioned transversely in the blood vessel so that it abuts on the wall in the manner of a ring. The plane of the loop is transverse, in particular rectangular, to the longitudinal direction of the main part 14. The loop thus has a size such that it abuts on the wall of a blood vessel from inside with a slight pressure. The outer diameter of the loop is about 4-6 mm.

Figure 2:
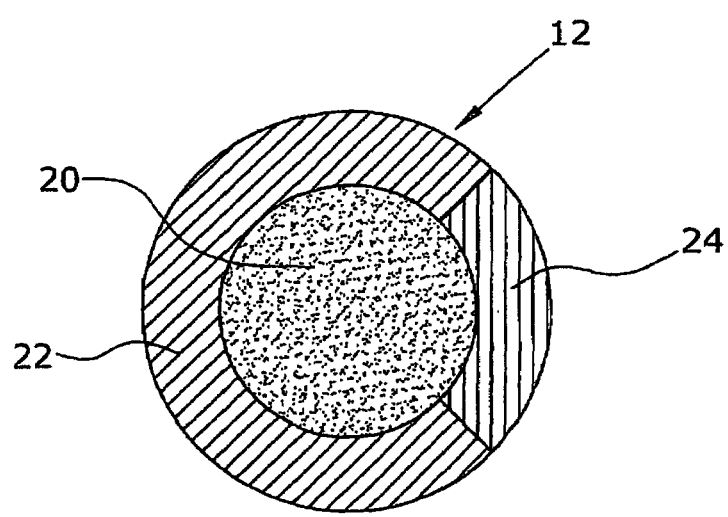
FIG. 2 is an up-scaled section along line II-II in FIG. 1.

FIG. 2 illustrates a cross section though the strand of the catheter 12. the strand includes a core which, in the present case, is formed by a single optical fiber 20, and a sheath 22 with a higher refraction index than the core. In the present embodiment, the sheath extends over a part of the circumference of the core that is greater than 270°. The remaining part of the circumference is formed by a decoupling portion 24 which, in the present case, is made of a material having a lower refraction index than the sheath 22. The radiation exit's the strand sideward from the segment of the decoupling portion 24. Thus, the radiation only exits toward one side of the circumference of the strand.

Figure 3:
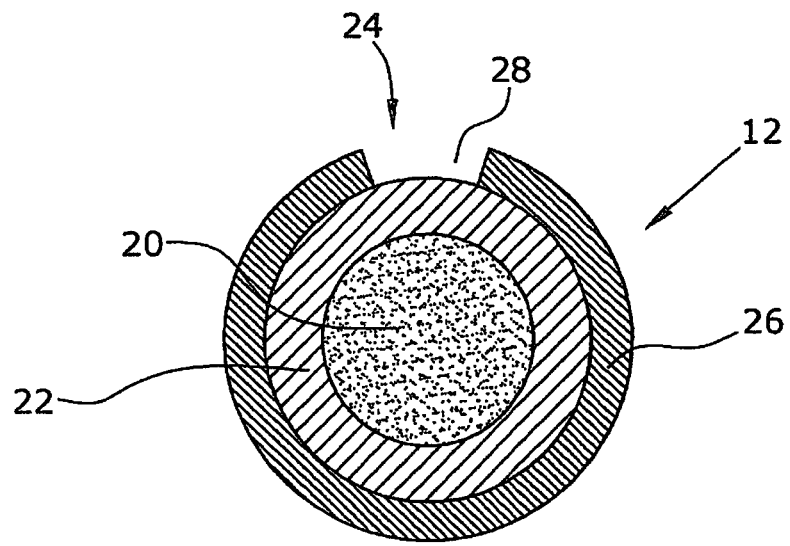
FIGS. 3-7 illustrate cross sections through further embodiments of the laser applicator.

FIG. 3 illustrates an embodiment in which the sheath 22 of light-transmissive material is enclosed by a reflective layer 26. The latter exposes a window 28 forming the decoupling portion 24, so that, here too, the light only exits at one point along the circumference.

Figure 4:
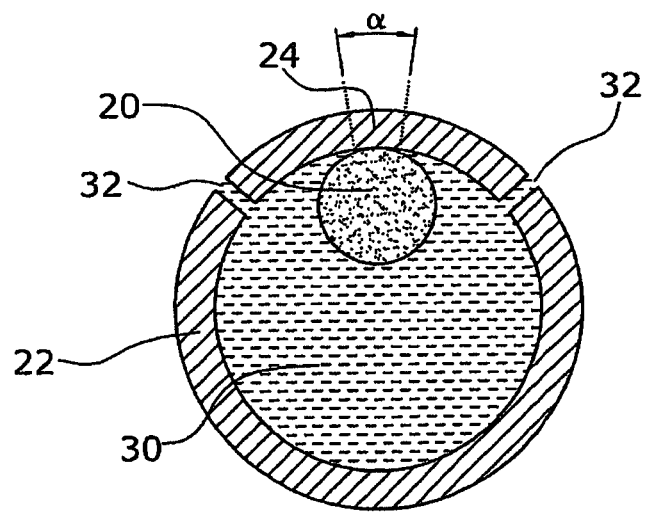

FIG. 4 illustrates an embodiment, in which the optical fiber directly abuts on the sheath 22 by a part of its circumference so that a boundary layer is formed between them at this point. The optical fiber 20 is arranged eccentrically in the sheath 22, and the free space forms a lumen 30 filled with a material having a low refraction index, such as water, for example. The sheath 22 comprises rinsing channels 32 through which the liquid can escape outward from the lumen 30.

The contact between the optical fiber 20 and the sheath 22 forms a lateral decoupling portion 24 with an aperture angle α.

Figure 5:
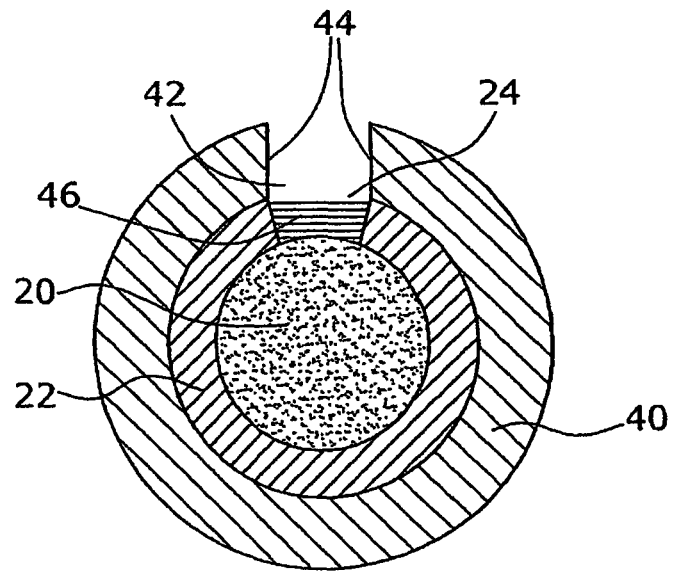

FIG. 5 illustrates an embodiment in which the sheath 22 of the optical fiber 20 is enclosed by an outer protective cladding 40. At the position of the decoupling portion 24, the protective cladding 40 is provided with a slot 42 whose wall is provided with a reflector layer 44. In the decoupling portion 24, the sheath 22 includes a diffuser 46 for the lateral decoupling of the laser energy.

Figure 6:
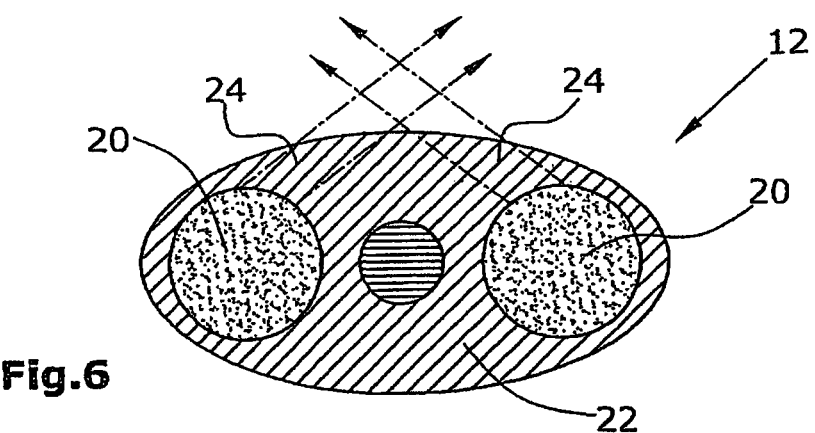

FIG. 6 illustrates a cross section through a catheter 12 which comprises a plurality of optical fibers 20 embedded in a sheath 22. The optical fibers 20, whose light exits from the sheath 22 at the decoupling portion 24, focus the decoupled laser light at a distance from the catheter 12, the maximum energy density being reached at the beam crossing point.

Figure 7:
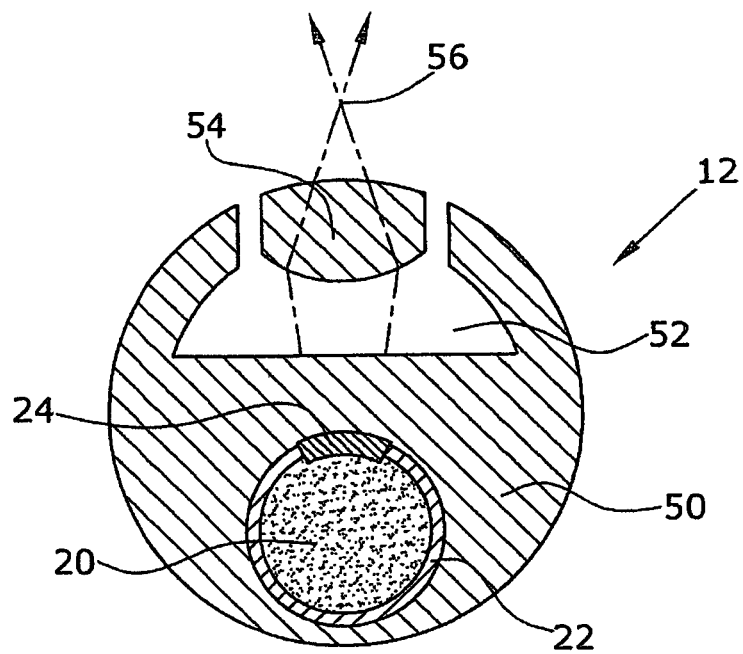

FIG. 7 illustrates a catheter 12 with an optical fiber 20 and a sheath 22, wherein the decoupling portion 24 is formed according to FIG. 2. The optical fiber is enclosed by an outer cladding 50 and arranged eccentrically therein. The outer cladding 50 comprises a lumen 52 that may contain a rinsing liquid, for example. The same has a lower refraction index than the outer cladding 50 so that the outer cladding forms a lens 54 through which the radiation decoupled from the decoupling portion 24 is focussed on a focal point 56.

Figure 8:
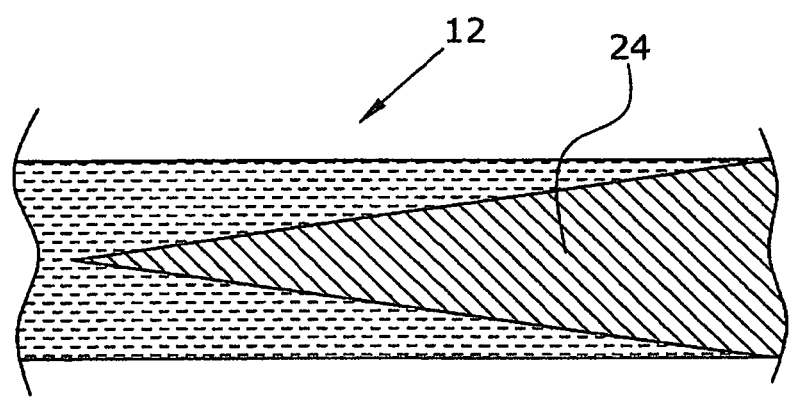
FIG. 8 is an illustration of a wedge-shaped decoupling region for obtaining a distribution of the decoupled energy that is uniform in the longitudinal direction.

FIG. 8 illustrates a catheter in which the decoupling portion 24 widens in the longitudinal direction of the catheter 12 so that, on the whole, the decoupling portion is almost wedge-shaped. Thereby, a uniform irradiation characteristic in the axial direction and a discontinuous irradiation in the radial direction are achieved.

What is claimed is:

1. A laser applicator with an elongate flexible catheter introducible into a blood vessel and including an optical fiber that extends in a flexible sheath with a part of a circumference of the optical fiber directly abutting the sheath with the optical fiber being arranged eccentrically in the sheath and defining a free space that forms a lumen between the sheath and the optical fiber, the lumen being filled with a material having a low refraction index, said sheath having a major straight section and a distal end section and a lateral decoupling portion in said distal end section, the sheath being preformed as a loop in the region of said distal end section said loop defining a plane, wherein the plane of the loop extends transverse to the major straight section of the sheath, the decoupling portion being configured to direct laser energy mainly or exclusively outward with respect to the loop, seen in the cross section of the sheath so that the loop abuts on the wall of the blood vessel circularly to heat surrounding tissue by the laser energy penetrating from the optical fiber into said tissue, wherein the catheter is stretchable to be advanced to a destination through a tube or over a guide wire.

2. The laser applicator of claim 1, wherein the loop describes a portion of more than 180°.

3. The laser applicator of claim 1, wherein the decoupling portion extends over less than 90° of the circumference of the optical fiber.

4. The laser applicator of claim 1, wherein the sheath is a tubular sheath.

5. The laser applicator of claim 4, wherein the sheath encloses said lumen for a light-refracting liquid in contact with the optical fiber.

6. The laser applicator of claim 5, wherein the sheath has lateral exit openings.

7. The laser applicator of claim 1, wherein the decoupling portion has a width increasing in the distal direction.

8. The laser applicator of claim 1, wherein the optical fiber comprises a plurality of optical fibers.

* * * * *